United States Patent [19]

Summers et al.

[11] Patent Number: 5,321,491
[45] Date of Patent: Jun. 14, 1994

[54] METHOD AND APPARATUS FOR GRADING SHELL EGGS

[75] Inventors: Ian R. Summers, Beecroft; Donald S. Bloser, Mount Pritchard; Blake R. Painter, Waverton, all of Australia

[73] Assignee: Ovascan Pty. Ltd., New South Wales

[21] Appl. No.: 856,058

[22] PCT Filed: Nov. 9, 1990

[86] PCT No.: PCT/AU90/00540
§ 371 Date: Jun. 11, 1992
§ 102(e) Date: Jun. 11, 1992

[87] PCT Pub. No.: WO91/07084
PCT Pub. Date: May 30, 1991

[30] Foreign Application Priority Data

Nov. 10, 1989 [AU] Australia ............. PJ7331

[51] Int. Cl.⁵ .............................. G01N 33/08
[52] U.S. Cl. .................. 356/53; 356/52; 356/56; 356/66; 356/67; 356/239; 209/524; 209/526; 382/43; 358/91
[58] Field of Search ............ 356/52, 53, 56, 66, 356/67, 237, 239; 209/524, 526, 939, 510, 511; 382/43; 358/101, 106

[56] References Cited

U.S. PATENT DOCUMENTS 2,636,925 6/1949 Gasciogne ............ 356/53
4,486,775 12/1984 Catlow ............ 358/106
4,624,367 11/1986 Shafer et al. ........... 382/43
4,805,778 2/1989 Nambu ............ 209/510

FOREIGN PATENT DOCUMENTS 479365 1/1977 Australia .
490867 4/1977 Australia .
486834 9/1977 Australia .
0200478 11/1986 European Pat. Off. .
0321981 6/1989 European Pat. Off. .
694958 12/1930 France .
2608899 12/1986 France .
59-151007 8/1984 Japan .
62-211544 4/1988 Japan .
921644 3/1963 United Kingdom .

Primary Examiner—Davis L. Willis
Assistant Examiner—La Charles Keesee
Attorney, Agent, or Firm—Welsh & Katz, Ltd.

[57] ABSTRACT

In the grading of shell eggs passing in a stream through a candling bed, images of the eggs are compared with image data characteristic of eggs of known grade so as to assign a grade to each egg in the stream. Positional information representative of the movement of the eggs is combined with the assigned grade to control a mechanical egg routing device. Images of multiple egg streams may be multiplexed and processed together. The images may be Fourier transformed before comparison.

20 Claims, 1 Drawing Sheet

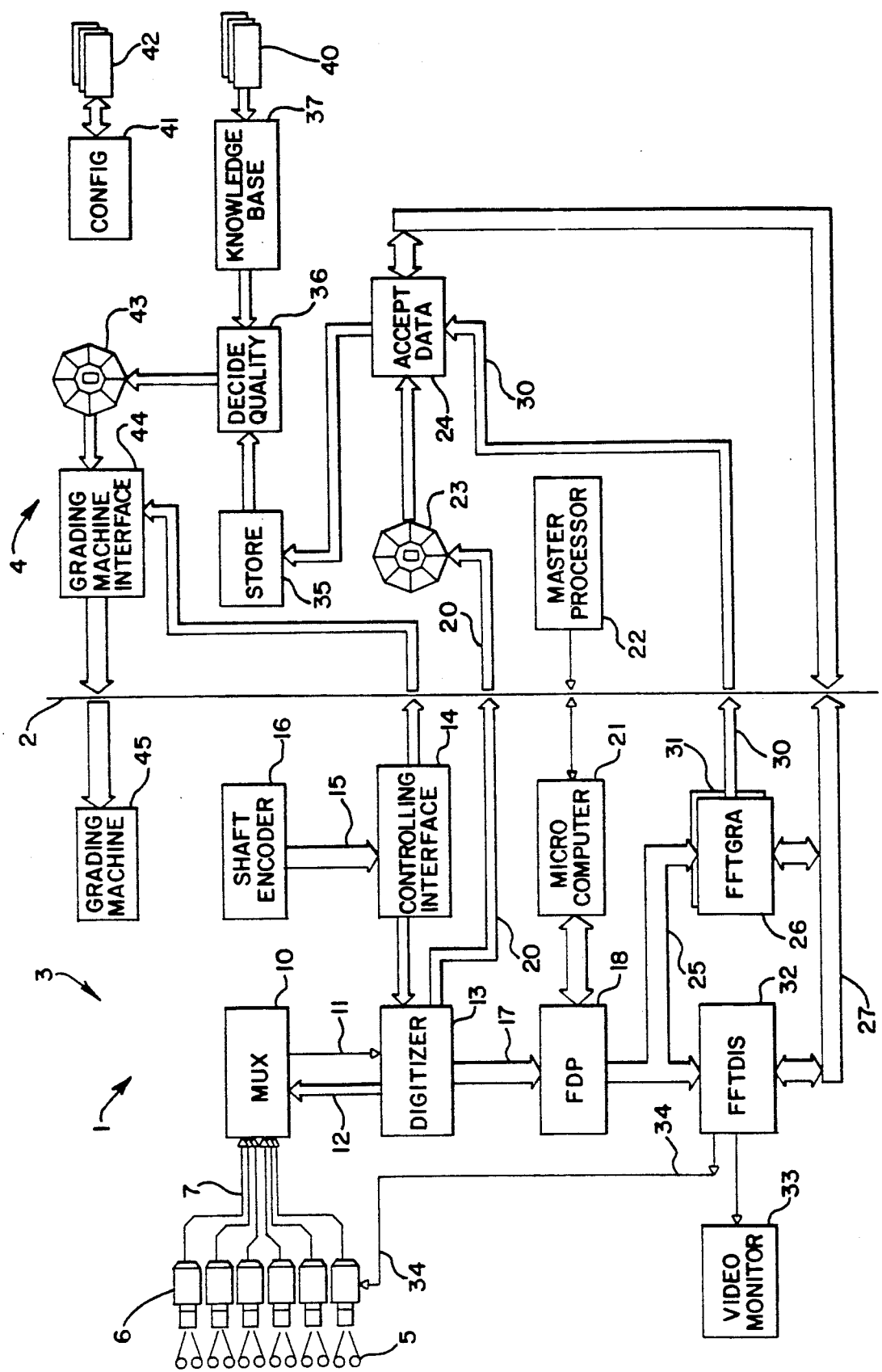

METHOD AND APPARATUS FOR GRADING SHELL EGGS

TECHNICAL FIELD

This invention relates to a method and apparatus for the grading of shell eggs contained in a moving stream. The invention is primarily intended for use with existing egg grading machines but is also able to form part of a purpose-built machine.

BACKGROUND ART

The inspection of eggs to assess their wholesomeness is an essential part of quality control. Modern egg handling and grading facilities have highly automated egg washing, weighing, grading and packaging equipment yet still depend to a large degree on human operators for the inspection and grading of the eggs. This operation is commonly referred to as candling.

The process of candling and the routing of eggs to selected lines for appropriate handling is well developed. Currently, operators visually identify faulty or flawed eggs in a moving stream of eggs passing through an inspection station, or candling booth, and with the aid of manual controls they notify the grading equipment to identify and route the eggs to the appropriate packing station.

By way of example, on a modern egg grading machine such as the "Diamond 8200" (Registered trade mark) automatic grader two operators view eggs as they are passed over high intensity lights while being slowly rotated. During this operation various faults or flaws are identified by the operators. Eggs that are "leakers" or broken pieces are removed by hand at the candling station. All others are either tagged or allowed to pass freely.

First quality (grade) eggs are allowed to flow directly to the main packing station, whilst defective or lesser grade eggs are allocated to one of up to four alternative packing stations. On the "Diamond 8200" grader, allocation of lesser grade eggs is performed within the candling booth using two wands, which are integrated with the grading machine control system. Each wand serves half the egg stream proceeding through the candling booth and is equipped with a finger grip at one end containing two buttons with a third button or "tip" located at its other extremity. To activate the wand, the "tip" is touched onto the surface of the egg to be graded by the operator. This action indicates a fault and when used in conjunction with the other two buttons, four categories can be identified. Similar systems of fault identification are used with other makes of automatic grading machines.

The disadvantages of current manual egg candling systems include:
(a) A full capacity system requires at least two highly skilled operators at any one time.
(b) Operators must be vigilant at all times; with flow rates in excess of 45000 eggs/hour the operators experience high levels of fatigue and occupational stress.
(c) Lack of attention or misjudgment allows undergrade eggs to pass, resulting in poor quality eggs reaching the marketplace. Often operators over-compensate and tend to "overpull" by routing first quality eggs to lesser grades, with consequential economic loss to the producer.

DISCLOSURE OF THE INVENTION

It is an object of this invention to provide a method and apparatus for grading shell eggs contained in a moving stream which will overcome, or at least ameliorate, one or more of the above disadvantages.

Accordingly, in one aspect this invention consists in an apparatus for grading shell eggs contained in a moving stream comprising means to generate image data characteristic of each egg shell and its contents; means to compare said image data with image data characteristic of eggs of known grade to assign a grade to each egg in said stream; reference means to provide a position signal indicative of the movement of said stream of eggs; and control means responsive to said grade assigned to each egg and to said position signal to provide an output signal for control of a mechanical egg routing device.

In a second aspect this invention consists in a method for grading shell eggs contained in a moving stream comprising the steps of generating image data characteristic of each egg shell and its contents; comparing said image data with image data characteristic of eggs of known grade to assign a grade to each egg in said stream; obtaining positional information indicative of the movement of said stream of eggs; and generating an output for control of a mechanical egg routing device from said grade assigned to each egg and said positional information.

In practice, this invention is preferably utilised in connection with an egg grading machine of known type such as the "Diamond 8200" described above. In such a system the eggs are conveyed in a continuous stream over a high intensity light source with a rolling action so that each egg can be viewed from a number of aspects.

The image data is preferably generated by means of a series of video cameras positioned above the egg stream to capture images of one or more eggs as they pass over the light source. Preferably the video cameras are switches so that their output signals are sequenced at the vertical blanking interval time of the video cameras such that a multiplexed composite video output from each of the cameras is represented as a single video signal. The timing of the multiplexing, or camera switching is preferably synchronised to the flow rate of the egg stream by means of a positional signal indicative of the movement of the egg stream. Such a positional signal can for example, be obtained from any suitable moving part of the conveyor system.

The multiplexed video signal is preferably digitised to produce a digital stream of image data and then processed to enhance the characteristic data. The processing preferably includes a fourier transform to convert the digitised image from the "time domain" to the "frequency domain". The image data is preferably further processed to effect a comparison with known data to determine whether the eggs fall within the nominated limits of various egg grades.

Preferably, the processing provides for adjustment of the parameters applied to the comparison to control the selection criteria for acceptance or rejection of individual eggs to various grades. Preferably, the control signal is interfaced to the control system of known grading equipment to operate the grading equipment to divert appropriate eggs to the selected packing stations.

It will therefore be apparent that this invention provides automated characterisation and recording of flaws and faults in shell eggs in a moving stream to high levels of certainty and in accordance with a predetermined selection criteria. By means of the output control signal generated, an identified egg can be allocated to the appropriate packing station for its assigned grade. Further, the data generated in relation to each egg can be stored for future analysis. Additionally, the invention enables the generation of a printout indicating the types of faults and flaws in eggs and the basis of the comparison of the data with known data. In this way a feedback control or a self teaching process in respect of the inspection process can be effected to continually improve the level of certainty of correct grading of the eggs.

Additionally, this invention provides a mechanism whereby eggs can be graded by weight and/or colour. Further, the invention can provide statistical data and totals of egg faults as well as identifying batch faults (that is faults attributable to an individual producer). The invention can also be utilised to examine other characteristics of eggs, for example the identification of fertile eggs in chicken hatcheries.

BRIEF DESCRIPTION OF THE DRAWINGS

One preferred embodiment of this invention will now be described, by way of example only, with reference to the accompany drawing, which is a schematic block diagram of an apparatus according to this invention.

MODE FOR CARRYING OUT THE INVENTION

The invention will be described in the form of an add on device for use with an existing egg grading machine such as the "Diamond 8200" automatic grader. It will however be appreciated that the invention can also be incorporated into a purpose-built machine using a conveying and diverting system of substantially conventional type as found in existing grading machines.

The egg grading machine (not shown) includes a conveying system which carries columnar streams of eggs over a high intensity light source known as a candling bed. The eggs are conveyed with a rolling action so that each egg can be viewed from a number of aspects as it passes over the candling bed. In the "Diamond 8200" machine there are twelve columns of eggs passing over the candling bed. An array of video cameras or image sensors is positioned in a selected formation across the egg stream so as to permit each camera to capture images of one or more columns of eggs as they pass over the candling bed. The preferred arrangement is a bank of 6 to 12 cameras which can scan up to 24 rows of eggs.

Referring particularly to FIG. 1, the egg grading apparatus 1 is shown divided by a dotted line 2 into a hardware portion 3 to the left and a (generally) software portion 4 to the right. It will be appreciated that such a division is in practice fairly arbitrary and will vary according to the particular embodiment. As shown in FIG. 1 the rows of eggs 5 are scanned by a bank of cameras 6 whose outputs 7 are transmitted to a video multiplexer unit 10 to provide a multiplexed analogue composite video signal 11. The multiplexer selects the output from each camera according to a sequence defined by control signals 12 output from a digitiser 13. The timing of the multiplexing is synchronised to the flow rate of the egg stream by a controlling interface 14 which receives positional information 15 from a shaft encoder 16. The switching of the multiplexer occurs at the vertical blanking interval time of the video cameras so that the composite video output from the multiplexer consists of complete images from each camera. Since the vertical blanking interval of the cameras occurs much more rapidly than the movement of the egg stream, it is possible to synchronise the switching of the multiplexer without losing overall synchronism with the moving eggs.

The shaft encoder responds to a rotating shaft (not shown) forming part of the egg conveying system.

The controlled sequential switching from one video camera to the next produces video images of the eggs which appear stationary despite the velocity of the egg stream. The digitiser 13 converts the analogue composite video signal 11, according to the timing imposed by controlling interface 14, into a stream of digital image data (A-BUS) 17 for processing by a Fourier data processor (FDP) 18. In conventionally known manner, the data transmitted via A-BUS 17 represents all the grey scales in the image frame as integers, typically 0 to 255.

It will be apparent that, in order to inspect 24 rows of eggs with 12 cameras, it is necessary to view more than one row with each camera. Accordingly, the video frames are divided into segments, each containing the image of one row, so that the signals transmitted via bus 17 include data for each segment. Typically, the segments are quadrants of the video frame. The effective result is to multiply the number of cameras at the expense of some image resolution. This sacrifice of resolution confers the important advantage that the Fourier transform is performed more rapidly. In the preferred embodiment each segment extracted from a video frame comprises 128×128 pixels and is sufficient to characterise the eggs.

The digitiser also outputs an identifying data stream via identifying bus (ID-BUS) 20 which indicates the source of each image of an egg included in the A-BUS 17 data stream transmitted to the FDP 18. Depending on the speed of the egg stream, a camera may capture a number of images of each egg in subsequent frames. For each egg, the ID-BUS 20 information includes the number of the camera which views the egg, the segment of the camera image which includes the egg, and whether there are multiple images of the particular egg. Since, as has been described, the eggs roll as they pass over the candling bed, subsequent images of the same egg may be different. The comparison of different images is performed by software and will be described below.

The FDP 18 unit performs a multi-dimensional Fourier transform on the A-BUS 17 data and is able to perform windowing and filtering to delete unwanted data and amplify the characteristic data to produce an enhanced image. The FDP unit is configured and controlled by a dedicated micro-computer 21 in communication with a master processor 22. In this way, computation intensive tasks are shared.

As the transformation of data in the FDP takes a finite time (strongly dependent on the resolution of the original image), the ID-BUS 20 data is passed to a buffer (ID-FIFO) 23 which delays the information so that it can later be married to the output of the FDP by an ACCEPT DATA software block 24 running in the master processor 22. The output of the FDP, via a vector bus (V-BUS) 25, comprises a stream of complex components from which are selected four complex components by an FFT component 'grabber' (FFTGRA) 26. The FFTGRA 26 selects components from the V-BUS data stream according to predefined parameters programmed by the master processor via a processor bus (P-BUS) 27. When the selected data is accumulated, an interrupt (IRQ-BUS) 30 informs the master processor. At this point the ACCEPT DATA software takes over the V-BUS data 25 and combines it with the ID-BUS data 20 delayed, as described above, in the ID-FIFO 23.

The FFTGRA element of the preferred embodiment is modular in nature so that more or less components can be extracted from the V-BUS data according to particular requirements. In order to extract more components for greater discrimination in the grading process, additional FFTGRA boards 31 may be included. In those circumstances a daisy chain interrupt structure is used for IRQ-BUS 30 in order to inform the master processor.

The V-BUS data is also directed to display circuitry (FFTDIS) 32, including a video monitor 33, so that the transformed data may be inspected. The cameras 6 are synchronised to FFTDIS by a sync signal 34 so that all images are stable.

In the preferred embodiment the display unit has access to both the V-BUS 25 and A-BUS 17 so that both transformed and untransformed data may be viewed. It should be noted that the display of information in this manner serves only to benefit operators of the egg grading machine and takes no part in the grading process.

The master processor 22 stores 35 the output of the ACCEPT DATA block 24 and compares it, in a DECIDE QUALITY block 36, with known data so as to categorise each egg into one of the selected grades. FIG. 1 depicts the sum of acquired knowledge about what characterises grades of eggs as a knowledge base block 37 having access to data files 40. In the comparison, represented by DECIDE QUALITY block 36, adjustment can be made to the parameters applied so as to control the criteria by which eggs are assigned a particular grade. That is, the grading can essentially be 'fine tuned' to account for observed and consistent departure from the grading required. In this portion of the software, also, the comparison of multiple images of the same egg mentioned earlier is resolved.

Similarly, the configuration information used to initialise and control such components as the FDP and FFTGRA are shown collectively in FIG. 1 as a configuration block 41 accessing configuration files 42. The statistical numbers of eggs assigned particular grades can be collected and utilised for further adjustment for the selection criteria.

Once a grade has been assigned to an egg by the DECIDE QUALITY block 36 details of lower grade eggs are passed to a buffer (BAD-FIFO) 43 to be delayed as the eggs pass through the machine and then to a grading machine interface 44 which provides an output to the control system of the grading equipment 45. The control system operates the mechanical routing devices associated with the known machine. In most machines first quality eggs are not diverted but simply pass along the conveyor to a final packing station whereas eggs falling into designated lesser grades are appropriately diverted to different packing stations.

The ranges of acceptable characteristic grades can be preset from prior analysis or extrapolation of the characteristic image data of eggs of various grades or alternatively a learn mode in which the characteristics of eggs in the stream are stored and an external input of the grade provided as a means of establishing the criteria for the assigning of grades.

The foregoing describes only one embodiment of this invention and modifications may be made thereto without departing from the scope of the invention.

We claim:

1. An apparatus for grading eggs contained in a moving stream comprising means to generate image data characteristic of each egg shell and its contents, said image data generating means including a candling bed over which the eggs are passed and said image data representing the interaction of light from the candling bed with the contents and shell of the egg and including data indicative of a defect in the contents or shell of the egg; processing means to process said image data and compare said processed image data with image data characteristic of eggs of known grade to assign a grade to each egg in said stream, said processing means comprising means to perform a fourier transform; reference means to provide a position signal indicative of the movement of said stream of eggs; and control means responsive to said grade assigned to each egg and to said position signal to provide an output signal for control of a mechanical egg routing device.

2. An apparatus as claimed in claim 1 wherein said image data is a video signal generated by one or more video cameras positioned adjacent said moving stream.

3. An apparatus as claimed in claim 2 including a plurality of said video cameras and a multiplexer switched at the vertical blanking interval of said cameras to generate a multiplexed output signal.

4. An apparatus as claimed in claim 3 wherein said position signal is used to synchronise the multiplexer to the egg stream.

5. An apparatus as claimed in claim 3 further comprising means to digitise said multiplexed output signal to produce a digitised output signal.

6. An apparatus as claimed in claim 4 further comprising means to digitize said multiplexed output signal to produce a digitized output signal.

7. An apparatus as claimed in claim 5 wherein said means to perform a fourier transform operates on said digitised output signal.

8. An apparatus as claimed in claim 7 wherein said means to digitise an output from said multiplexer provides data block identification information to said processing means for identification of the data corresponding to selected images from the fourier transformed signal.

9. An apparatus as claimed in claim 8 wherein said data block identification information is delayed before being provided to said processing means to compensate for the fourier transform processing time.

10. An apparatus as claimed in any one of the preceeding claims wherein said position signal is provided by a shaft encoder responsive to the rotation of a shaft forming part of a conveyor for said moving stream.

11. A method for grading eggs contained in a moving stream comprising the steps of:
    passing the eggs over a candling bed and capturing image data representing the interaction of light from the candling bed with the contents and shell of the egg and including data indicative of a defect in the contents or shell of the egg;
    processing said image data by means of a fourier transform;
    comparing said processed image data with image data characteristic of eggs of known grade to assign a grade to each egg in said stream;

obtaining a position signal indicative of the movement of said stream of eggs; and generating an output signal for control of a mechanical egg routing device from said grading assigned to each egg and said position signal.

12. A method as claimed in claim 11 wherein said image data is a video signal generated by means of one or more cameras positioned adjacent said moving stream.

13. A method as claimed in claim 12 further comprising the step of multiplexing outputs from a plurality of said video cameras and switching said multiplexer at the vertical blanking interval of said cameras to provide a multiplexed signal.

14. A method as claimed in claim 13 further comprising the step of using said position signal to synchronise said multiplexing with the movement of said egg stream.

15. A method as claimed in claim 13 further comprising the step of digitising said multiplexed signal and to produce a digitised signal.

16. A method as claimed in claim 15 further including the step of performing a fourier transform on the digitised signal.

17. A method as claimed in claim 16 further comprising the step of providing data block identification information for identification of data corresponding to selected images from said fourier transformed signal.

18. A method as claimed in claim 17 further including the step of delaying said data block identification information to compensate for the fourier transform processing time.

19. A method as claimed in claim 11 further including the step of obtaining said position signal from a shaft encoder responsive to the rotation of a shaft forming part of a conveyor for said moving stream.

20. A method as claimed in claim 14 further comprising the step of digitizing said multiplexed signal and to produce a digitized signal.

* * * * *